United States Patent [19]

Hirai et al.

[11] Patent Number: 5,455,372
[45] Date of Patent: Oct. 3, 1995

[54] METHOD OF PRODUCING A GLYCOLIC ACID ESTER

[75] Inventors: Koichi Hirai; Yasuo Nakamura; Yasunori Fukuda, all of Ube, Japan

[73] Assignee: Ube Industries, Ltd., Yamaguchi, Japan

[21] Appl. No.: 209,386

[22] Filed: Mar. 10, 1994

[30] Foreign Application Priority Data

Mar. 12, 1993 [JP] Japan .................................. 5-052299
Jun. 29, 1993 [JP] Japan .................................. 5-159247

[51] Int. Cl.⁶ .................................................. C07C 69/675
[52] U.S. Cl. ........................................................ 560/179
[58] Field of Search ............................................. 560/179

[56] References Cited

U.S. PATENT DOCUMENTS 4,112,245 9/1978 Zehner et al. .......................... 568/864
4,409,395 10/1983 Miyazaki et al. ....................... 560/179
4,585,890 4/1986 Miyazaki et al. ....................... 560/179

FOREIGN PATENT DOCUMENTS 0057007 8/1982 European Pat. Off. .
2031883 2/1983 United Kingdom .
2031883 2/1983 United Kingdom .

*Primary Examiner*—José G. Dees
*Assistant Examiner*—Barbara S. Frazier
*Attorney, Agent, or Firm*—Burgess, Ryan & Wayne

[57] ABSTRACT

A glycolic acid ester is produced by hydrogenating an oxalic acid diester of the formula, $(COOR)_2$, wherein R is a $C_{1-6}$ alkyl group, with hydrogen in the presence of a solid catalyst comprising, for example, copper and silver metals carried on a solid carrier, and in the additional presence of an aliphatic alcohol, and collecting the resultant glycolic acid ester from the reaction mixture by distillation, preferably in the presence of an ester of a $C_{3-12}$ dicarboxylic acid.

20 Claims, 2 Drawing Sheets

1

METHOD OF PRODUCING A GLYCOLIC ACID ESTER

BACKGROUND OF THE INVENTION

1. Field of the Invention

The present invention relates to a method of producing a glycolic acid ester.

More particularly, the present invention relates to a method of producing a glycolic acid ester by a catalytic hydrogenation of an oxalic acid diester with a high selectivity and with a high yield.

The glycolic acid esters are significantly useful as a material for cleaning agent for a boiler and the like, an additive for plating, an etching agent and an tanning agent for leather and an intermediate for preparing detergent builders and for biodegradable polymers.

2. Description of the Related Art

As a method for producing a glycolic acid ester, a catalytic reaction method of an oxalic acid diester, for example, diethyl oxalate with hydrogen in the presence of a catalyst is known from, for example, Japanese Examined Patent Publication (Kokoku) No. 55-42971, U.S. Pat. No. 4,112,245, and German Patent No. 459,603. The method as disclosed in those publications is disadvantageous in that since the reaction is a successive reaction, if the catalyst used and the reaction conditions applied are not optimum, the reaction proceeds excessively so that an undesirable ethylene glycol is produced as a by-product and thus the selectivity of the desired glycolic acid ester is reduced. Also, the by-product causes the isolation and collection of the desired glycolic acid ester to be complicated.

To solve the above-mentioned problem, for example, in GB-B-2,031,883, it was attempted to catalytically react an oxalic acid diester with hydrogen in the presence of a catalyst comprising at least one member selected from ruthenium, nickel and Raney nickel under specific reaction conditions. By this method, a reaction product comprising one of ethylene glycol and glycolic acid ester in a relatively large amount is obtained.

However, to industrially produce glycolic acid ester, the above-mentioned method must be improved so that the reaction rate is enhanced and the selectivity of glycolic acid ester is increased. Also, it is necessary that a cheap catalyst is allowed to be used and the reaction conditions are made mild.

U.S. Pat. No. 4,585,890 discloses a catalyst, in which an amine complex of copper is carried on a silica carrier, for the catalytic reaction. Also, U.S. Pat. No. 4,409,395 discloses a catalyst in which silver or palladium is carried on a carrier, for the catalytic reaction. However, those catalysts are unsatisfactory in that the catalytic activity of the catalysts and the resultant selectivity of glycolic acid ester are low and thus they are not appropriate for practical use.

As mentioned above, the conventional methods for producing the glycolic acid ester are disadvantageous in that since the hydrogenation of an oxalic acid diester is effected by a successive reaction, the progress of the reaction causes an undesirable production of ethylene glycol as a by-product, and thus the resultant glycolic acid ester is obtained with a poor selectivity thereof.

Accordingly, a new method of producing a glycolic acid ester by a Catalytic reaction with an enhanced selectivity of the glycolic acid ester and with a high yield, is needed.

SUMMARY OF THE INVENTION

An object of the present invention is to provide a method of producing a glycolic acid ester by a catalytic hydrogenation reaction of an oxalic acid diester with a high selectivity of glycolic acid ester and with a high yield.

Another object of the present invention is to provide a method of producing a glycolic acid ester by a catalytic hydrogenation reaction of an oxalic acid diester under mild reaction conditions.

Still another object of the present invention is to provide a method of producing a glycolic acid ester by a catalytic hydrogenation reaction of an oxalic acid diester, in which method the resultant glycolic acid ester can be easily separated and collected from the reaction mixture.

The above-mentioned object can be attained by the method of the present invention which comprises the steps of:

hydrogenating an oxalic acid diester of the formula (I):

$$(COOR)_2 \qquad (I)$$

wherein R represents a lower alkyl group having 1 to 6 carbon atoms, with hydrogen in the presence of a solid catalyst and in the additional presence of at least one aliphatic alcohol, and collecting the resultant glycolic acid ester from the reaction mixture.

In the method of the present invention, the solid catalyst preferably comprises a solid carrier and a catalytic component carried on the carrier and comprising at least copper metal and silver metal.

The catalytic component preferably comprises 5 to 50% by weight of copper metal and 0.1 to 20% by weight of silver metal based on the weight of the solid carrier.

Also, in the method of the present invention, preferably the aliphatic alcohol has 1 to 6 carbon atoms, and is present in an amount of 5 molar parts or more per molar part of the oxalic acid diester.

Further, in the collecting step of the method of the present invention, the reaction product of the hydrogenating step, which comprises the resultant glycolic acid ester and a remaining fraction of nonreacted oxalic acid diester, is subjected to distillation in the presence of an ester of dicarboxylic acid having 3 to 12 carbon atoms, to selectively distill and collect the glycolic acid ester from the reaction mixture; and a resultant distillation residue comprising a mixture of the non-reacted oxalic acid diester fraction with the ester of dicarboxylic acid having 3 to 12 carbon atom is withdrawn in the form of a liquid from the distillation system.

DESCRIPTION OF THE PREFERRED EMBODIMENTS

Figure 1:
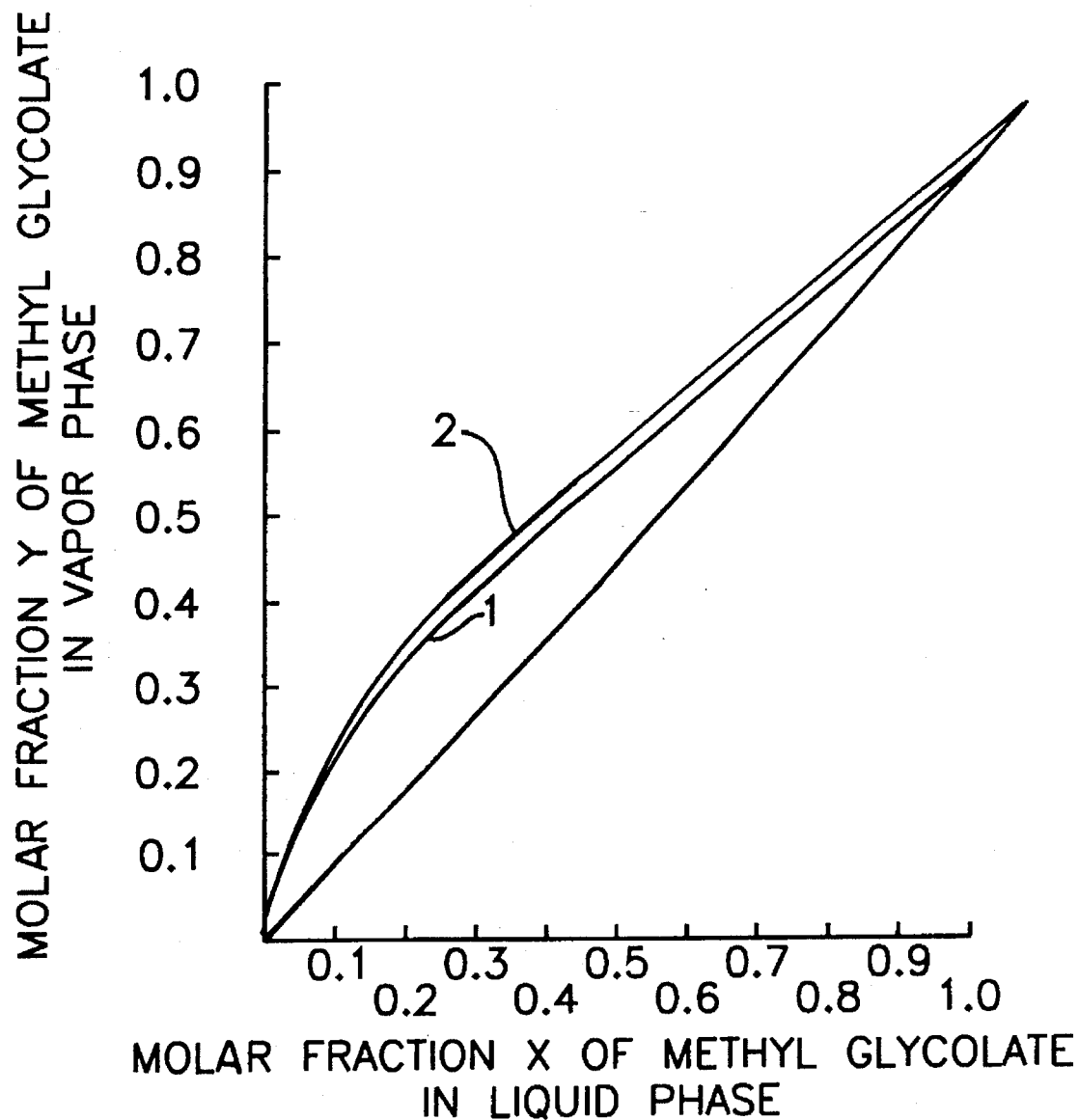
FIG. 1 is a diagram showing a vapor-liquid equilibrium curve ① of a two component system consisting of methyl glycolate and dimethyl oxalate and a vapor-liquid equilibrium curve ② of a three component system consisting of methyl glycolate, dimethyl oxalate and dimethyl adipate.

In the method of the present invention, the hydrogenation reaction of an oxalic acid diester with hydrogen in gas phase in the presence of a solid catalyst and in the additional presence of an aliphatic alcohol effectively renders the resultant glycolic acid ester to be produced with a high selectivity and with a high yield thereof.

In the method of the present invention, the oxalic acid diester is selected from those of the formula (I):

$$(COOR)_2 \qquad (I)$$

wherein R represents a member selected from alkyl groups having 1 to 6 carbon atoms, for example, methyl, ethyl, propyl, butyl, amyl (pentyl) and hexyl groups.

The oxalic acid diester is converted to a glycolic acid ester in accordance with the following reaction:

$$(COOR)_2 + 2H_2 \rightarrow ROOC-CH_2OH + ROH$$

The hydrogenating step is preferably carried out in a gas phase. In an embodiment of the hydrogenerating step, the oxalic acid disester may be present in a liquid phase.

The oxalic acid diester can be prepared by diesterifying oxalic acid with an aliphatic monohydric alcohol having 1 to 6 carbon atoms.

Preferably, the oxalic acid diester usable for the method of the present invention is selected from dimethyl oxalate, diethyl oxalate, dipropyl oxalates, dibutyl oxalates and diamyl oxalate. More preferably, the oxalic acid diester is selected from diester of oxalic acid with aliphatic monohydric alcohols having 1 to 4 carbon atoms, more preferably from dimethyl oxalate and diethyl oxalate.

The solid catalyst usable for the present invention comprises a solid carrier and a catalytic component carried on the solid carrier. The catalytic component is preferably present in an amount of 0.01 to 50%, more preferably 5 to 50% by weight, based on the weight of the solid carrier.

The solid catalyst usable for the method of the present invention preferably comprises a solid carrier and a catalytic component carried on the solid carrier and comprising at least one member selected from the group consisting of copper group (Ib group) metals, for example, copper and silver, iron group (VIII group) metals, for example, iron, nickel and cobalt, and platinum group (VIII group) metals, for example, platinum, palladium, ruthenium and rhodium. The catalytic component may comprise a member selected from compounds of copper with at least one other metal, for example, chromium, zinc and silver.

The solid carrier useable for the method of the present invention preferably comprises at least one member selected from diatomaceous earth, activated carbon, silicon carbide, titania, alumina, silica-alumina, lanthanoid, zirconia and zinc oxide. Preferably, in the catalyst usable for the present invention comprises a catalytic component comprising at least one member selected from copper, silver, ruthenium and copper-chromium compound and carried on the above-mentioned solid carrier.

The solid catalyst usable for the method of the present invention can be prepared by providing an aqueous solution of at least one member selected from watersoluble compounds of the above-mentioned metals, for example, halides such as chlorides, bromides, iodides and, fluorides, inorganic acid salts, for example, nitrates, sulfates, and phosphates, organic acid salts, for example, acetates, and complexes, of the above-mentioned metals; causing the aqueous metal compound solution to be carried on the solid carrier; and reducing the metal compound or complex carried on the solid carrier by using a reducing agent, for example, hydrogen gas.

The method of carrying the aqueous metal compound solution on the solid carrier is not limited to a specific method, and can be selected from conventional methods, for example, impregnation method (immersion-adsorption method), knead-mixing method, evaporation-dry-solidification method, and coprecipitation method. For the method of the present invention, the co-precipitation method, impregnation method and the evaporation-dry-solidification method are preferable because those methods can be easily carried out by simple operation. For example, in the co-precipitation method, the solid carrier in the form of particles or grains is dispersed in the aqueous solution of the metal compound; an aqueous solution of an alkalizing agent, for example, sodium hydroxide, potassium hydroxide, sodium carbonate, ammonium carbonate or ammonia is added little by little to the aqueous metal compound solution to cause a precipitate comprising the metal compound to deposit on the carrier, and then the carrier carrying thereon the metal compound-containing precipitate is separated and collected from the aqueous system by way of filtration or concentration. When two or more different metal compounds are used, the carrying procedure may be carried out in one single operation for all the metal compounds or in two or more separate operations for each of the metal compounds.

The reduction of the metal compounds on the carrier is carried out by fully washing the precipitate with water, drying the washed precipitate in air at a temperature of around 120° C. and then subjecting the dried precipitate to a reduction reaction with a usual reduction agent, for example, a hydrogen gas or hydrazine.

In the reduction procedure for the metal compounds using the hydrogen gas, it is preferable that before the hydrogenating procedure for the oxalic acid diester, the precipitate is reduced with a usual hydrogen gas at a temperature of 150° C. to 400° C. for a reducing time of from 1 to 2 hours, to prepare the solid catalyst comprising the catalytic metal component carried on the solid carrier.

In the reduction product of the metal compounds, even if non-reduced metal compound remains in an amount of 20% or less, preferably 10% or less, based on the total weight of the catalytic component, on the carrier, the resultant catalyst can be employed for the hydrogenating step of the oxalic acid diester without any disadvantages.

The catalyst for the present invention may be in the form of a fine powder, grains or shaped pellets. The size of the catalyst particles, grains or pellets is not limited to a specific range of size usually, the fine powder has a particle size of 20 to 100 μm, the grains have a 4 to 200 mesh size (4750 to 75 μm) and the shaped pellets have a size of 0.47 to 20 mm.

In the method of the present invention, it is important that the catalytic hydrogenating step of the oxalic acid diester be carried out in the presence of at least one aliphatic alcohol.

The aliphatic alcohol used for the hydrogenating step effectively enhances the selectivity and yield of the glycolic acid ester.

To make the isolation and collection of the resultant glycolic acid ester easy, the aliphatic alcohol is preferably selected from aliphatic monohydric alcohols having 1 to 6 carbon atoms and being provided with the same alkyl group as that of the oxalic acid diester used as a starting material for the method of the present invention. Namely, where dimethyl oxalate is employed as a starting material, the aliphatic alcohol is preferably methyl alcohol, and where diethyl oxalate is employed as a starting material, ethyl alcohol is preferably added to the hydrogenating system.

The aliphatic alcohol to be present in the hydrogenating system is preferably in an amount of 5 molar parts or more, more preferably 8 to 20 molar parts, per mole of the oxalic acid diester. If the molar ratio of the aliphatic alcohol to the oxalic acid diester is more than 20, sometimes the reaction rate of the hydrogenation is undesirably reduced, the amount of energy necessary to isolate and collect the resultant reaction product becomes undesirably large, and thus an economical disadvantage occurs.

The aliphatic alcohol may be mixed with the oxalic acid diester to be used as a starting material before the hydrogenating step, or may be fed into the hydrogenating system through a supply line different from that of the oxalic acid diester.

In the method of the present invention, the catalytic hydrogenating reaction of the oxalic acid diester is preferably carried out at a temperature of from 100° C. to 300° C., more preferably from 150° C. to 250° C. under a pressure of from the ambient atmospheric pressure to 50 kg/cm²G. Also, in hydrogenating step, the hydrogen and the oxalic acid diester are present preferably in a molar ratio of 2:1 to 100:1, more preferably 4:1 to 50:1 ($H_2/(COOR)^2$).

Further, in the hydrogenating step, the mixture gas of hydrogen with oxalic acid diester is brought into contact with the solid catalyst preferably for a contact time of 0.01 to 20 seconds, more preferably 0.2 to 8 seconds.

In an embodiment of the method of the present invention, the catalyst for the hydrogenating reaction of the oxalic acid diester comprises a solid carrier comprising at least one member selected from the group consisting of silica, alumina, titania, zirconia, diatomaceous earth, zinc oxide, lanthanum oxide and activated carbon, and a catalytically active component carried on the carrier and comprising at least copper metal and silver metal.

The catalyst optionally comprises at least one additional member selected from copper compounds and silver compounds.

The copper and silver compounds are preferably selected from halides, nitrates, sulfates, phosphates and acetates of copper and silver.

The catalytic component preferably comprises the copper metal and optionally the copper compound in a total amount, in terms of copper metal, of 5 to 50%, more preferably 5 to 30% by weight, and the silver metal and optionally the silver compound in a total amount, in terms of silver metal, of 0.01 to 20%, more preferably 0.02 to 10% by weight, based on the weight of the solid carrier.

The catalyst can be produced by the same method as mentioned above.

The resultant catalyst containing at least copper metal and silver metal and optionally the copper and/or silver compound may further comprise at least one metal other than copper and silver metals and at least one metal compound other than the copper and silver compounds.

The copper and silver metal-containing catalyst can maintain the catalytic activity, for example, a high space-time yield thereof at a high level, for the catalytic hydrogenation reaction of the oxalic acid diester over a long period of reaction time. Also, this type of catalyst has a high mechanical strength and thus can be stably employed over a long period of time without degradation thereof.

In the method of the present invention, preferably, the hydrogen gas and a vapor of the oxalic acid diester are mixed with and diluted by a vapor of the aliphatic alcohol or an inert gas, for example, a nitrogen gas, and the mixed gas is brought into contact with the solid catalyst placed in a hydrogenating reactor. The composition of the mixed gas is not limited to a specific composition. For example, the oxalic acid diester is dissolved in a concentration of 10 to 40%, preferably 15 to 35% by weight in the aliphatic alcohol, the resultant solution is vaporized and the resultant vapor is introduced together with the hydrogen gas into a reactor containing the catalyst therein.

In the method of the present invention, after the hydrogenation reaction is completed, the resultant reaction mixture, which comprises the aimed glycolic acid ester and a remaining fraction of non-reacted oxalic acid diester, is subject to the collecting step of the glycolic acid ester from the reaction mixture.

In this collecting step, the glycolic acid ester can be isolated and collected from the reaction mixture by any conventional methods, for example, cooling, distillation and extraction methods.

As mentioned above, in the method of producing a glycolic acid ester by a catalytic hydrogenation reaction of the oxalic acid diester with hydrogen, the resultant reaction mixture comprises the desired glycolic acid ester and a remaining fraction of non-reacted oxalic acid diester. Accordingly, it is indispensable to separate the glycolic acid ester from the non-reacted oxalic acid diester fraction. For example, to collect methyl glycolate produced by a catalytic hydrogenation of dimethyl oxalate, it is necessary to isolate the methyl glycolate from the non-reacted dimethyl oxalate in the resultant reaction mixture. Also, when ethyl glycolate is produced by a catalytic hydrogenation of diethyl oxalate, the ethyl glycolate is necessarily isolated from the non-reacted diethyl oxalate fraction contained in the resultant reaction mixture.

Referring to FIG. 1, curve ① shows a relationship between a molar fraction X of methyl glycolate in liquid phase and a molar fraction Y of methyl glycolate in vapor phase in a two component mixture of methyl glycolate with dimethyl oxalate. Also, in FIG. 1, curve ② shows a relationship between a molar fraction X of methyl glycolate in liquid phase and a molar fraction Y of methyl glycolate in vapor phase in a three component mixture of methyl glycolate with dimethyl oxalate and dimethyl adipate.

Curve ① shows that when a molar fraction of methyl glycolate in the two component mixture is 90% or more under a vapor-liquid equilibrium condition, the molar fraction of the liquid phase methyl glycolate is very close to the molar fraction of the vapor phase methyl glycolate. Therefore, it is very difficult to isolate methyl glycolate from the two component mixture by way of usual distillation.

In a conventional method, a glycolic acid ester is produced by converting formaldehyde to a carbonyl compound. In this conventional method, various attempts were made to collect the resultant glycolic acid ester from the reaction mixture.

For example, U.S. Pat. No. 2,152,852 discloses a method in which a catalyst is removed from a reaction mixture, and thereafter, glycolic acid is collected from the reaction mixture by a crystallization precipitation. Also, German Patent No. 240,542 discloses a method in which glycolic acid ester is collected by an azeotropic distillation using a solvent consisting of dichloromethane, to eliminate alcohol from the resultant reaction mixture.

However, those known methods are not appropriate for collecting in a simple operation, glycolic acid ester from a reaction mixture obtained by a hydrogenation reaction of oxalic acid diester and thus containing the resultant glycolic acid ester mixed with a remaining fraction of non-reacted oxalic acid diester, due to the specific behavior of the glycolic acid ester as shown by the curve ① in FIG. 1.

However, referring to FIG. 1, where dimethyl adipate is added to the two component mixture to provide a three component mixture, curve ② shows that even when a molar fraction of methyl glycolate in the three component mixture is 90% or more under a vapor-liquid equilibrium condition, the molar fraction of the vapor phase methyl glycolate is significantly higher than the molar fraction of the liquid phase methyl glycolate.

Namely, in the three component mixture, the glycolic acid ester exhibits a high relative volatility, and thus the vapor phase glycolic acid ester can be easily isolated as a distillate from the three component mixture by the distillation procedure.

In an embodiment of the method of the present invention, the resultant reaction product from the hydrogenating step is subjected to distillation in the presence of an ester of dicarboxylic acid having 3 to 12 carbon atoms, to selectively distill and collect the glycolic acid ester from the reaction mixture, and a resultant distillation residue comprising a mixture of the non-reacted oxalic acid diester fraction and the ester of $C_{3-12}$ dicarboxylic acid is withdrawn in the form of a liquid from the distillation system.

In a preferable procedure for collecting the glycolic acid ester, the resultant reaction mixture from the hydrogenating step is subjected to a preliminary distillation for removing the aliphatic alcohol and then to a principal distillation in which the ester of $C_{2-12}$ dicarboxylic acid is added to the remaining mixture containing the glycolic acid ester and the non-reacted oxalic acid diester, and the resultant three component mixture is distilled to selectively evaporate the glycolic acid ester.

As described above, in the three component mixture of glycolic acid ester with oxalic acid diester and the ester of $C_{3-12}$ dicarboxylic acid, the glycolic acid ester exhibits a high relative volatility and thus can be withdrawn as a vapor from the top of a distiller. Also, oxalic acid diester exhibits a low relative volatility and thus can flow down together with the ester of $C_{3-12}$ dicarboxylic acid through the distiller and then the mixture of tho oxalic acid diester with the ester of $C_{3-12}$ dicarboxylic acid is withdrawn in the state of a liquid from the bottom of the distiller.

Generally, the mixture of the oxalic acid diester with the ester of $C_{3-12}$ dicarboxylic acid is subjected to a further distillation to collect the oxalic acid diester as a distillate from the mixture, and the distillation residue comprising the ester of $C_{3-12}$ dicarboxylic acid is withdrawn in the state of a liquid from the distiller. The withdrawn ester of $C_{3-12}$ dicarboxylic acid can be recycled to the collecting step and re-used for the collection of the glycolic acid ester.

The ester of $C_{3-12}$ dicarboxylic acid usable for the method of the present invention is preferably selected from the group consisting of diesters of aliphatic ester of $C_{3-12}$ dicarboxylic acid having 3 to 12 carbon atoms, more preferably 4 to 10 carbon atoms, with aliphatic monohydric alcohols having 1 to 4 carbon atoms. Preferably, the aliphatic dicarboxylic acid for the ester of $C_{3-12}$ dicarboxylic acid is selected from the group consisting of malonic acid, succinic acid, glutaric acid, adipic acid, pimelic acid, suberic acid, azelaic acid, brassylic acid and dodecanedioic acid. Also, the aliphatic monohydric alcohol for the ester of $C_{3-12}$ dicarboxylic acid is preferably selected from methyl alcohol, ethyl alcohol, propyl alcohols and butyl alcohols, Namely, the ester of $C_{3-12}$ dicarboxylic acid is preferably selected from malonic acid diesters, for example, dimethyl malonate and diethyl malonate, succinic acid diesters, for example, dimethyl succinate and diethyl succinate, glutaric acid diesters, for example, dimethyl glutarate and diethyl glutarate, adipic acid diesters, for example, dimethyl adipate and diethyl adipate, pimelic acid diesters, for example, dimethyl pimelate and diethyl pimelate, suberic acid diesters, for example, dimethyl suberate and diethyl suberate, azelaic acid diesters, for example, dimethyl azelate and diethyl azelate, brassylic acid diesters, for example, dimethyl brassylate and diethyl brassylate, and dodecanedioic acid diesters, for example, dimethyl dodecanedioate and diethyl dodecanedioate.

In the collection step, to enhance the collection efficiency of the glycolic acid ester, the ester of $C_{3-12}$ dicarboxylic acid is added to the reaction mixture to such an extent that the molar fraction of the ester of $C_{3-12}$ dicarboxylic acid in the three component mixture is at a level of 0.1 or more, more preferably 0.2 or more. In view of the collection efficiency of the glycolic acid ester, the amount of the ester of $C_{3-12}$ dicarboxylic acid ester to be added to the reaction mixture has no upper limit and is set forth in consideration of industrial usability and economical effect. An increase in content of the ester of $C_{3-12}$ dicarboxylic acid in the three component mixture effectively causes a difference in relative volatility between the components to be separated from each other to increase, the theoretical distillation stage number of the distiller to decrease, the necessary size of distiller to be reduced and the cost of the distiller to become low. However, the large content of the ester of $C_{3-12}$ dicarboxylic acid in the three component mixture causes such disadvantages that a necessary amount of heat for the distillation and the necessary diameter of the distiller become large, and the recovery cost of the ester of $C_{3-12}$ dicarboxylic acid becomes high. Therefore, the amount of the ester of $C_{3-12}$ dicarboxylic acid to be used in the collecting step is set forth so that the collection cost and efficiency become optimum.

The distiller usable for the collecting step of the method of the present invention is preferably selected from Oldasho type multistage distiller and packing type distiller, more preferably the packing type distiller which exhibit a low pressure loss. The distillation is carried out usually under a reduced pressure.

Figure 2:
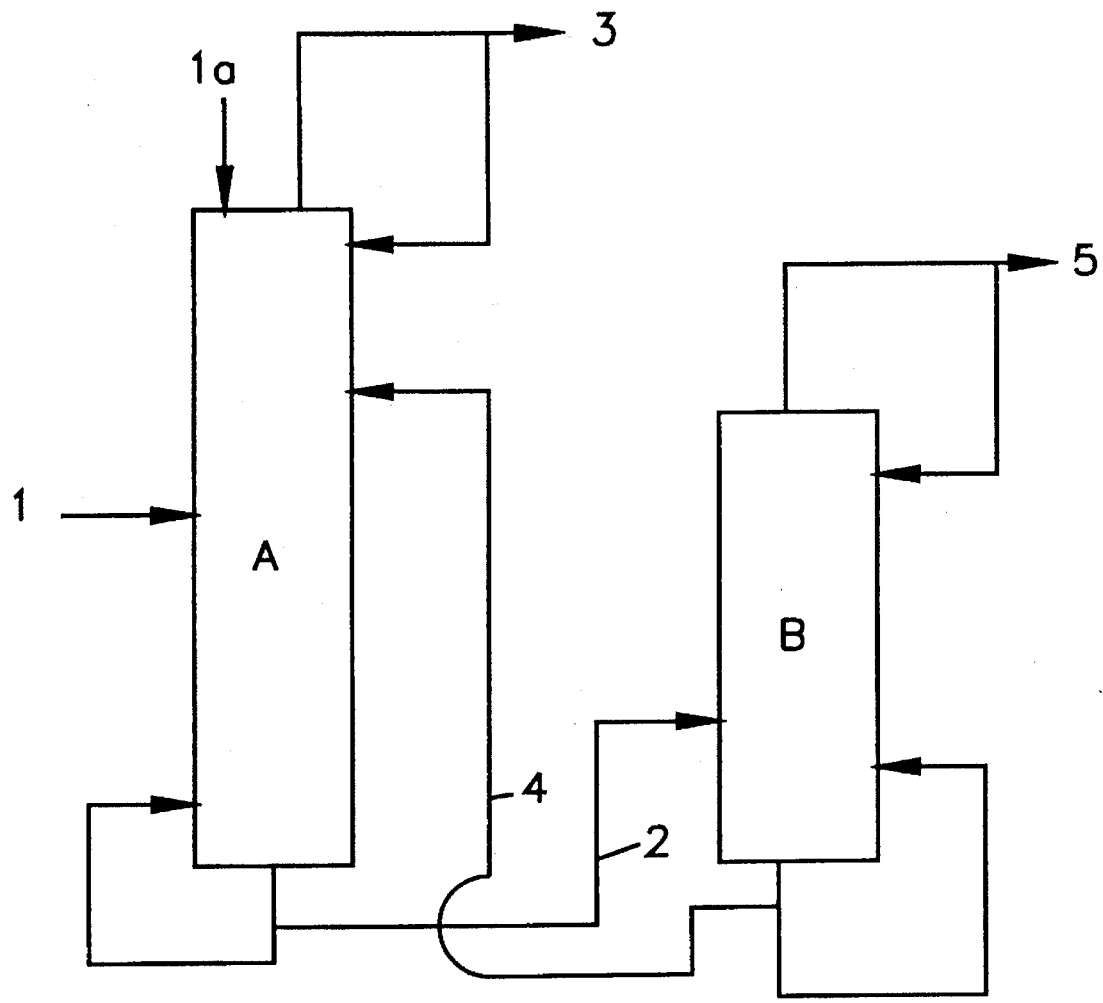
FIG. 2 shows a distillation system for collecting a glycolic acid ester from a reaction mixture produced by a hydrogenating step of the method of the present invention.

An industrial procedure of the distillation for collecting the glycolic acid ester is carried out by using a continuous distillation apparatus as shown in FIG. 2. For example, a reaction mixture 1 supplied from the hydrogenating step and comprising the resultant glycolic acid ester, for example, methyl glycolate and a remaining fraction of non-reacted oxalic acid diester, for example, dimethyl oxalate, is continuously fed into a first distillation column A, while continuously feeding a solution of an ester of $C_{3-12}$ dicarboxylic acid, for example, dimethyl adipate, into the first distillation column A through a top inlet 1a thereof. In this case, the dimethyl adipate may be mixed with the reaction mixture 1 in the outside of the distillation column A and continuously fed together with the reaction mixture 1 into the first distillation column A. The liquid contained in the first distillation column A is heated at a distillation temperature at which methyl glycolate is vaporized. The methyl glycolate is continuously distilled while refluxing around the top outlet of the column. The vaporized methyl glycolate is withdrawn as a distillate 3 from the first distillation column A so as to isolate it from the distillation mixture.

A residual liquid 2 of the first distillation column A comprises a mixture of dimethyl oxalate and dimethyl adipate is withdrawn from the first distillation column A through a bottom outlet thereof and continuously fed into a second distillation column B. The liquid contained in the second distillation column B is continuously distilled while refluxing the resultant vapor around a top outlet thereof. The resultant dimethyl oxalate vapor is withdrawn as a distillate 5 from the second distillation column B through a top outlet thereof.

The residual liquid 4 of the second distillation column B comprises dimethyl adipate and is withdrawn from the second distillation column B through a bottom outlet thereof. The withdrawn dimethyl adipate is returned to the first distillation column B and re-used therein.

By using the distillation apparatus as shown in FIG. 2, the isolation and collection of glycolic acid ester, the recovery of the residual fraction of the non-reacted oxalic acid diester, and the recycling and re-use of the ester of $C_{3-12}$ dicarboxylic acid can be continuously carried out.

As mentioned above, in the three component mixture of the glycolic acid ester with the oxalic acid diester and the ester of $C_{3-12}$ dicarboxylic acid, even when the molar fraction of the glycolic acid ester in a two component system consisting of the glycolic acid ester and the oxalic acid diester is 90% or more, the difference in vapor-liquid equilibrium composition between the glycolic acid ester and the oxalic acid diester becomes significantly large as shown by a curve ② in FIG. 1, and thus the glycolic acid ester is easily isolated as a distillate from the three component mixture by a first distillating procedure, and then the oxalic acid diester is easily isolated as a distillate from the residual liquid of the first distillation by a second distillating procedure. The remaining liquid in the second distillation comprising the ester of $C_{3-12}$ dicarboxylic acid can be returned to the collecting step and re-used for the first distillation.

EXAMPLES

The method of the present invention will be further illustrated by way of specific examples which are merely representative and in no way restrict the scope of the present invention.

In the examples, a liquid space velocity (LHSV, g/ml.hr), a space velocity (SV, $hr^{-1}$), and contact time (CT, sec) were determined in accordance with the following equations.

Liquid space velocity (LHSV) in $g/ml \cdot hr =$ $$\frac{\text{Feeding rate of oxalic acid diester in g/hr}}{\text{Volume of calalyst in ml}}$$

Space velocity (SV) in $hr^{-1} =$ $$\frac{\frac{\text{Feeding rate in}}{\text{liter/hr of } A} \times \frac{273 + \text{reaction temperature in °C.}}{273}}{\text{Volume of catalyst in liter}}$$

wherein A represents a mixture of an oxalic acid diester with an aliphatic alcohol, hydrogen and nitrogen.

$$\text{Contact time } (CT) \text{ in sec} = \frac{1}{SV} \times 3600$$

wherein SV is as defined above.

Also, in the examples, a conversion in % of an oxalic acid diester, a selectivity in % of a glycolic acid ester, a selectivity in % of ethylene glycol and a space time yield (STY) of a glycolic acid ester were determined in accordance with the following equations.

Conversion (%) of oxalic acid diester =

$$\frac{\text{Molar amount of reacted oxalic acid diester}}{\text{Total amount of supplied oxalic acid diester}} \times 100$$

Selectivity (%) of glycolic acid ester =

-continued $$\frac{\text{Molar amount of produced glycolic acid ester}}{\text{Molar amount of reacted oxalic acid diester}} \times 100$$

Selectivity (%) of ethylene glycol =

$$\frac{\text{Molar amount of produced ethylene glycol}}{\text{Molar amount of reacted oxalic acid diester}} \times 100$$

Space time yield (STY) of glycolic acid ester =

$$LHSV \times \frac{\text{Conversion of oxalic acid diester}}{1000} \times \frac{\text{Selectivity of glycolic acid ester}}{100} \times$$

$$\frac{\text{Molecular weight of glycolic acid ester}}{\text{Molecular weight of oxalic acid diester}} \times 100$$

EXAMPLE 1

Preparation of catalyst

A precursory catalyst in which a copper amine complex was carried on a silica carrier was prepared in the following manner which was the same as that disclosed in Japanese Examined Patent Publication (Kokoku) No. 60-45,938 (U.S. Pat. No. 4,585,890) Examples 8 to 10.

An aqueous solution was prepared by dissolving 38.0 g of cupric nitrate trihydrate ($Cu(NO_3)_2 \cdot 3H_2O$) in 200 ml of water, and 60 ml of a concentrated aqueous ammonia solution was added to the aqueous cupric nitrate solution to adjust the pH of the resultant solution to a level of from 11 to 12. A deep blue-colored solution containing a copper-amine complex was obtained.

To this deep blue-colored solution, 66.6 g of a 30 weight % aqueous colloidal silica sol were added, and the resultant mixture was stirred at room temperature for several hours. Then, the temperature of the mixture was raised to evaporate away almost all of the water in the mixture and the resultant mixture was further dried at a temperature of 120° C. for 12 hours.

The dried product was fully washed with water, the washed product was dried in the ambient air atmosphere at a temperature of 140° C. for 14 hours. The resultant precursory catalyst was subjected to a reduction treatment in a hydrogen gas stream at a temperature of 350° C. for 2 hours. The resultant copper metal-containing solid catalyst was crushed to prepare catalyst grains having a size of 1 to 2 mm.

Preparation of methyl glycolate

A glass-made gas phase reaction tube having an inside diameter of 20 mm and a length of 700 mm was filled with 10 ml of the catalyst mentioned above. The catalyst-filled reaction tube was vertically placed in an electric furnace and heated therein while controlling the temperature of the catalyst layer in the reaction tube to a level of 220° C. Dimethyl oxalate in the state of a liquid was fed into an evaporator at the liquid space velocity (VLSV) as shown in Table 1, and the resultant dimethyl oxalate vapor was mixed with a hydrogen gas. The mixed gas of hydrogen with dimethyl oxalate vapor in a mixing molar ratio of 25:1 was fed together with 0.75 g/ml.hr of methyl alcohol into the catalyst-filled reaction tube through a top inlet of the tube at the space velocity (SV) as shown in Table 1 under the ambient atmospheric pressure, to catalytically hydrogenate dimethyl oxalate in the presence of methyl alcohol.

A reaction mixture passed through the reaction tube flowed through an ice-cooled trap and then the cooled reaction mixture was collected in the state of a liquid. The collected liquid was subjected to a gas chromatographic analysis. From the analysis results, the conversion of dimethyl oxalate, the selectivity and space time yield (STY) of methyl glycolate and the selectivity of ethylene glycol were determined. The results are shown in Table 1.

Comparative Example 1

The same procedures as in Example 1 were carried out with the following exceptions, No methyl alcohol was employed.

A mixed gas of hydrogen and dimethyl oxalate in a mixing molar ratio of 25.0:1 was fed together with a nitrogen gas at a liquid space velocity (LHSV) and a space velocity (SV) as shown in Table 1 into the reaction tube filled with 10 ml of the same catalyst as in Example 1. The hydrogenation reaction was carried out at a temperature of the catalyst layer of 220° C. under the ambient atmospheric pressure.

The results are shown in Table 1.

Example 2

Preparation of catalyst

A catalyst comprising silver metal carried on a silica carrier was prepared in the following manner which was the same as described in Japanese Examined Patent Publication (Kokoku) No. 62-37,030 (U.S. Pat. No. 4,409,395), Example 1.

An aqueous solution was prepared by dissolving 5 g of silver nitrate in 20 ml of water, and the resultant solution was added with 145 g of a 33 weight % aqueous colloidal silica sol. To the silica sol, an aqueous solution of 1.24 g of sodium hydroxide in 10 ml of water was gradually added.

After the addition was completed, the resultant mixture was aged at room temperature for one hour, and the resultant precipitate was collected by filtration. The filtered solid product consisting essentially of AgOH—$SiO_2$ was washed with water twice and dried at a temperature of 140° C. for one night to provide a precursory catalyst. The precursory catalyst in an amount of 2g was added with 40 ml of a 3% hydrazine aqueous solution and the resultant mixture was left to stand in the ambient air atmosphere for one night to reduce the silver compound. The reduced catalyst was collected from the mixture by filtration. The filtrate was washed with water, dried at room temperature under vacuum, and then further dried at a temperature of from 150° C. to 200°C., to provide a silver metal-containing catalyst.

The above-mentioned catalyst-preparation procedures were repeated to provide 20 g of the catalyst. The resultant catalyst was crushed to provide catalyst grains having a size of 1 to 2 mm.

Preparation of methyl glycolate

The same procedures as mentioned in Example 1 were carried out with the following exceptions.

The catalyst as mentioned in Example 1 was replaced by the catalyst as described above, and a mixed gas of hydrogen and dimethyl oxalate in a mixing molar ratio of 25.0:1 was fed together with methyl alcohol in a feed rate of 0.75 g/ml.hr, into the reaction tube containing therein 10 ml of the above-mentioned catalyst at a space velocity (Sv) as shown in Table 1. The liquid space velocity (LHST) of dimethyl oxalate was as indicated in Table 1. The catalytic hydrogenation reaction of dimethyl oxalate was carried out at a catalyst temperature of 249° C. under the ambient atmospheric pressure.

The results are shown in Table 1.

Comparative Example 2

Preparation of methyl glycolate

The same procedures as in Example 1were carried out with the following exceptions.

No methyl alcohol was employed.

A mixed gas of hydrogen and dimethyl oxalate in a mixing molar ratio of 25.0:1 was fed together with a nitrogen gas at a liquid space velocity (LHSV) and a space velocity (SV) as shown in Table 1 into the reaction tube filled with 10 ml of the same catalyst as in Example 2. The hydrogenation reaction was carried out at a temperature of the catalyst layer of 249° C. under the ambient atmospheric pressure.

The results are shown in Table 1.

Example 3

Preparation of ethyl glycolate

The same procedures as in Example 1 were carried out with the following exceptions.

The glass reaction tube was replaced by a stainless steel reaction tube, and the catalyst of Example 1 was replaced by a copper-chromium catalyst which was available under the trademark of Catalyst ST-205 from Sakai Kagaku K.K.

A mixed gas consisting of hydrogen and diethyl oxalate in a mixing molar ratio of 25.0:1 was fed together with ethyl alcohol in a feeding rate of 2.31 g/ml.hr at a space velocity (Sv) as shown in Table 1 into the reaction tube filled with 25 ml of the above-mentioned catalyst. The liquid space velocity (LHSV) of diethyl oxalate was as indicated in Table 1. The hydrogenation reaction of diethyl oxalate was carried out at a catalyst temperature of 190° C. under a reaction pressure of 20 kg/$cm^2$G.

The results are shown in Table 1.

Comparative Example 3

The same procedures as in Example 3 were carried out with the following exceptions.

The same stainless steel reaction tube and 25 ml of the catalyst as mentioned in Example 3 were employed. No ethyl alcohol was employed.

A mixed gas of hydrogen and diethyl oxalate in a mixing molar ratio of 25.0:1 was fed together with a nitrogen gas at a space velocity (SV) as shown in Table 1 into the reaction tube filled with 25 ml of the same catalyst as in Example 3. The liquid space velocity (LHSV) of diethyl oxalate was as indicated in Table 1. The hydrogenation reaction of diethyl oxalate was carried out at a catalyst temperature of 190° C. under a reaction pressure of 20 kg/$cm^2$G.

The results are shown in Table 1.

TABLE 1

| Example No. | Hydrogenation conditions | | | | | | Results | | | |
|---|---|---|---|---|---|---|---|---|---|---|
| | Temperature (°C.) | Pressure (kg/cm²G) | Hydrogen/ oxalic acid diester molar ratio | Aliphatic alcohol (g/ml · hr) | LHSV (g/ml · hr) | SV (hr⁻¹) | Conversion of oxalic acid diester (%) | Selectivity of glycolic acid ester (%) | Selectivity of ethylene glycol (%) | STY of glycolic acid ester |
| Example 1 | 220 | 0(*)1 | Dimethyl oxalate 25 | Methanol 0.75 | 0.25 | 3170 | 58.5 | 76.0 | 12.9 | 85 |
| Comparative Example 1 | 220 | 0(*)1 | Diemthyl oxalate 25 | Nitrogen | " | " | 57.3 | 69.2 | 15.4 | 76 |
| Example 2 | 249 | 0(*)1 | Dimethyl oxalate 25 | Methanol 0.75 | " | 3320 | 36.4 | 80.3 | 3.6 | 56 |
| Comparative Example 2 | 249 | 0(*)1 | Dimethyl oxalate 25 | Nitrogen | " | " | 36.0 | 57.0 | 4.0 | 39 |
| Example 3 | 190 | 20 | Diethyl oxalate 25 | Ethanol 2.31 | 0.80 | 7300 | 55.4 | 62.4 | 34.4 | 197 |
| Comparative Example 3 | 190 | 20 | Diethyl oxalate 25 | Nitrogen | " | " | 58.2 | 48.8 | 43.2 | 162 |

Note:
*1The ambient atmospheric pressure

Examples 4 to 7

Preparation of Catalyst

In each of Example 4 to 7, a precursory catalyst, in which a copper compound and a silver compound were carried on a silica carrier, was prepared in the following manner.

An aqueous solution was prepared by dissolving 39.2 g of cupric nitrate trihydrate ($Cu(NO_3)_2 \cdot 3H_2O$) and 2.1 g of silver nitrate ($AgNO_3$) in 200 ml of water, and 66.6 g of a silica sol (which was available under a trademark of Cataloid S30L, from Shokubai Kasei K.K.) were added to the solution and the resultant mixture was stirred.

To this mixture, a solution of 14.4 g of ammonium carbonate in 85 ml of water was gradually added dropwise over a time of 30 minutes while stirring the mixture. After the dropwise addition was completed, the reaction mixture was aged at room temperature for 1.5 hours while stirring. The resultant precipitate was isolated by filtration. The isolated precipitate was washed with 500 ml of water and filtered. The washing and filtering operations were repeated three times. The resultant bluish white cake was collected and dried at a temperature of 140° C. for 12 hours. A precursory solid catalyst containing the copper compound and the silver compound carried on the silica carrier was obtained.

The precursory solid catalyst was subjected to a reduction treatment in a hydrogen gas stream at a temperature of 350° C. for 2 hours.

A copper metal and silver metal-containing solid catalyst in the form of grains having a size of 1 to 2 mm was obtained.

Preparation of methyl glycolate

A glass-made gas phase reaction tube having an inside diameter of 20 mm and a length of 700 mm was filled with 20 ml of the catalyst mentioned above. The catalyst-filled reaction tube was vertically placed in an electric furnace and heated therein while controlling the temperature of the catalyst layer in the reaction tube to the level as shown in Table 2. Dimethyl oxalate was fed into an evaporator at the liquid space velocity (LHSV) as shown in Table 2, and the resultant dimethyl oxalate vapor was mixed with a hydrogen gas. The mixed gas of hydrogen with dimethyl oxalate in a mixing molar ratio of 2:1 to 12.3:1 was fed together with methyl alcohol into the catalyst-filled reaction tube through a top inlet of the tube at a space velocity (SV) and for a contact time (CT) as shown in Table 1 under the ambient atmospheric pressure, to catalytically hydrogenate dimethyl oxalate. The dimethyl oxalate was fed in the state of a solution in a concentration of 25% by weight in the methyl alcohol.

A reaction mixture passed through the reaction tube was cooled by and collected in an ice-cooled trap. The collected liquid was subjected to a gas chromatographic analysis. From the analysis results, the conversion of dimethyl oxalate, the selectivity and space time yield (STY) of methyl glycolate and the selectivity of ethylene glycol were determined.

The results are shown in Table 2.

Example 8

In 200 ml of water, 19 g of cupric nitrate ($Cu(NO_3)_2 \cdot 3H_2O$) and 2.3 g of silver nitrate ($AgNO_3$) were dissolved, and the solution was heated at a temperature of 75° C. to 80° C., The solution was mixed with 66.5 g of a silica sol (Cataloid S30L), and the mixture was stirred.

A solution of 7 g of sodium hydroxide in 200 ml of water was gradually added dropwise to the mixture over a period of 30 minutes, while stirring. After the dropwise addition was completed, the resultant reaction mixture was aged at room temperature for 2 hours. The resultant precipitate was collected by filtration. The collected precipitate was washed with water and filtered. The washing and filtering operations were repeated twice. The resultant cake was collected and dried at a temperature of 140° C. for 12 hours, to provide a precursory solid catalyst containing the copper compound and the silver compound carried on the silica carrier.

The precursory solid catalyst was subjected to a reduction treatment in a hydrogen stream at a temperature of 350° C.

for 2 hours. A solid catalyst containing copper metal and silver metal carried on the silica carrier was obtained in the form of grains having a size of 1 to 2 mm.

Preparation of methyl glycolate

The same procedures as in Example 4 were carried out with the following exceptions.

The above-mentioned catalyst was employed in place of the catalyst of Example 4.

A hydrogen gas and a vapor of a solution of 25% by weight of dimethyl oxalate in methyl alcohol was fed in a mixing molar ratio of hydrogen to dimethyl oxalate of 22.1:1 to the reaction tube containing 10 ml of the catalyst at a space velocity (SV) and for a contact time (CT) as shown in Table 2.

The liquid space velocity (LHSV) of dimethyl oxalate was as indicated in Table 2.

The catalytic hydrogenation reaction of dimethyl oxalate was carried out at a catalyst temperature of 237° C. under the ambient atmospheric pressure in the same manner as in Example 4.

The results are shown in Table 2.

Example 9

Preparation of catalyst

An aqueous solution of 19 g of cupric nitrate $(Cu(NO_3)_2.3H_2O)$ and 2.1 g of silver nitrate $(AgNO_3)$ dissolved in 200 ml of water was mixed with 60 ml of a 25 weight % aqueous ammonia solution. To the mixed solution, 66.5 g of a silica sol (Cataloid S30L) was added and the mixture was stirred. The resultant mixture was aged at room temperature for one hour while stirring. Then the a mixture was concentrated using a hot bath at a temperature of 80° C. to 90° C. The resultant precipitate was isolated by filtration and washed with 200 ml of water. The washing and filtering operations were repeated four times.

The resultant cake was collected, dried at a temperature of 120° C. for 12 hours, and fired at a temperature of 500° C. for 3 hours, to provide a solid catalyst precursor containing the copper compound and the silver compound carried on the silica carrier.

The catalyst precursor was subjected to a reduction treatment at a temperature of 350° C. for 2 hours, to provide a solid catalyst containing reduced copper metal and silver metal carried on the silica carrier. The catalyst is in the form of grains having a size of 1 to 2 mm.

Preparation of methyl glycolate

The same procedures as in Example 4 were carried out with the following exceptions.

The catalyst of Example 4 was replaced by the catalyst as mentioned above.

A mixed gas of hydrogen gas with a vapor of a solution of 25% by weight of dimethyl oxalate in methyl alcohol in which mixture the hydrogen and the dimethyl oxalate are in a mixing molar ratio of 5.65:1, was fed into the reaction tube containing therein 10 ml of the catalyst at a space velocity (SV) and for a contact time (CT) as indicated in Table 2.

The liquid space velocity (LSV) of dimethyloxalate was as indicated in Table 2.

The catalytic hydrogenation reaction of dimethyl oxalate was carried out at a catalyst temperature of 225° C. under the ambient atmospheric pressure in the same manner as in Example 4.

The results are shown in Table 2.

Example 10

Preparation of catalyst

The same catalyst preparation procedures as in Example 8 were carried out except that silver nitrate $(AgNO_3)$ was employed in an amount of 0.0633 g.

The resultant solid catalyst contained about 20% by weight of copper metal and about 0.16% by weight of silver metal.

Preparation of methyl glycolate

The same methyl glycolate preparation procedures as in Example 4 were carried out with the following exceptions.

The solid catalyst mentioned above was employed in place of the catalyst of Example 4.

A hydrogen gas and a vapor of a solution of 25% by weight of dimethyl oxalate in methyl alcohol were fed into the reaction tube containing therein the solid catalyst in an amount of 20 ml, whale controlling the molar ratio of hydrogen to dimethyl oxalate to a level of 12.3:1, at a space velocity (SV) and for a contact time (CT) as shown in Table 2.

The liquid vapor velocity (LHSV) of dimethyl oxalate was as indicated in Table 2.

The catalytic hydrogenation reaction of dimethyl oxalate was carried out at a catalyst temperature of 230° C. under the ambient atmospheric pressure in the same manner as in Example 4.

The results are shown in Table 2.

Example 11

Preparation of ethyl glycolate

The same procedures as in Example 4 were carried out with the following exceptions.

The same catalyst as in Example 4 was employed in an amount of 20 ml.

The dimethyl oxalate used in Example 4 was replaced by diethyl oxalate.

A hydrogen gas and a vapor of a solution of 25% by weight of diethyl oxalate in ethyl alcohol were fed into the reaction tube containing therein 20 ml of the catalyst, while controlling the molar ratio of hydrogen to diethyl oxalate to a level of 12.021, at a space velocity (SV) and for a contact time (CT) as shown in Table 2.

The liquid space velocity (LHSV) of diethyl oxalate was as indicated in Table 2.

The catalytic hydrogenation reaction of diethyl oxalate was carried out at a catalyst temperature of 220° C. under the ambient atmospheric pressure in the same manner as in Example 4.

The results are shown in Table 2,

Example 12

Preparation of butyl glycolate

The same procedures as in Example 4 were carried out with the following exceptions.

The same catalyst as in Example 4 was employed in an amount of 20 ml.

The dimethyl oxalate used in Example 4 was replaced by dibutyl oxalate.

A hydrogen gas and a solution of 25% by weight of dibutyl oxalate in butyl alcohol were fed into the reaction tube containing therein 20 ml of the catalyst, while controlling the molar ratio of hydrogen to dibutyl oxalate to a level of 12.0:1 at a space velocity (SV) and for a contact time (CT) as shown in Table 2.

The liquid space velocity (LHSV) of diethyl oxalate was as indicated in Table 2.

The catalytic hydrogenation reaction of dibutyl oxalate was carried out at a catalyst temperature of 220° C. under the ambient atmospheric pressure in the same manner as in Example 4.

The results are shown in Table 2.

Example 13

Preparation of methyl glycolate

The same procedures as in Example 4 were carried out with the following exceptions.

The same catalyst as in Example 4 was employed in an amount of 20 ml.

No methyl alcohol was employed.

A mixture of hydrogen, dimethyl oxalate and nitrogen were fed into the reaction tube containing therein 20 ml of the catalyst, while controlling the molar ratio of hydrogen to dimethyl oxalate to a level of 12.0:1 at a space velocity (SV) and for a contact time (CT) as shown in Table 2.

The liquid space velocity (LHSV) of dimethyl oxalate was as indicated in Table 2.

The catalytic hydrogenation reaction of diethyl oxalate was carried out at a catalyst temperature of 216° C. under the ambient atmospheric pressure in the same manner as in Example 4.

The results are shown in Table 2.

Comparative Example 4

Preparation of methyl glycolate

The same procedures as in Example 4 were carried out with the following exceptions.

The same catalyst as in Example 1 was employed in an amount of 100 ml.

No methyl alcohol was employed.

A hydrogen gas and dimethyl oxalate in a molar ratio of 25:1 were fed together with a nitrogen gas into the reaction tube containing therein 10 ml of the catalyst at a space velocity (SV) and for a contact time (CT) as shown in Table 2.

The liquid space velocity (LHSV) of dimethyl oxalate was as indicated in Table 2.

The catalytic hydrogenation reaction of dimethyl oxalate was carried out at a catalyst temperature of 220° C. under the ambient atmospheric pressure in the same manner as in Example 4.

The results are shown in Table 2.

Comparative Example 5

Preparation of methyl glycolate

The same procedures as in Example 4 were carried out with the following exceptions.

The same catalyst as in Example 2 was employed in an amount of 10 ml.

No methyl alcohol was used.

A hydrogen gas and dimethyl oxalate in a molar ratio of 25:1 were fed together with a nitrogen gas into the reaction tube containing therein 10 ml of the catalyst, at a space velocity (SV) and for a contact time (CT) as shown in Table 2.

The liquid space velocity (LHSV) of dimethyl oxalate was as indicated in Table 2.

The catalytic hydrogenation reaction of dimethyl oxalate was carried out at a catalyst temperature of 249° C. under the ambient atmospheric pressure in the same manner as in Example 4.

The results are shown in Table 2.

TABLE 2

| | | Hydrogenation conditions | | | | | Results | | | |
|---|---|---|---|---|---|---|---|---|---|---|
| Example No. | Temperature (°C.) | Pressure (kg/cm$^2$G) | Molar ratio $H_2$/(COOR)$_2$ | LHSV (g/ml·hr) | CT (sec) | SV (hr$^{-1}$) | Conversion of (COOR)$_2$ (%) | Selectivity of COOR–CH$_2$OH / CH$_2$OH (%) | Selectivity of CH$_2$OH–CH$_2$OH (%) | STY of COOR–CH$_2$OH (g/l·hr) |
| Example | | | | | | | | | | |
| 4 | 216 | 0*$^1$ | (R: methyl) 12.0/1 | 0.267 | 1.70 | 2120 | (R: methyl) 59.0 | (R: methyl) 94.5 | 4.2 | 113.8 |
| 5 | 222 | 0*$^1$ | (R: methyl) 12.0/1 | 0.276 | 1.64 | 2200 | (R: methyl) 80.1 | (R: methyl) 86.8 | 6.7 | 146.4 |
| 6 | 228 | 0*$^1$ | R: methyl 12.3/1 | 0.385 | 1.10 | 3270 | (R: methyl) 70.2 | (R: methyl) 88.9 | 7.4 | 183.3 |
| 7 | 247 | 0*$^1$ | R: methyl 12.3/1 | 0.386 | 1.07 | 3360 | (R: methyl) 90.2 | (R: methyl) 76.0 | 8.3 | 202.7 |
| 8 | 237 | 0*$^1$ | R: methyl 22.1/1 | 0.538 | 0.55 | 6500 | (R: methyl) 75.7 | (R: methyl) 85.0 | 4.3 | 264.0 |
| 9 | 225 | 0*$^1$ | R: methyl 5.65/1 | 0.538 | 1.09 | 3300 | (R: methyl) 66.9 | (R: methyl) 87.2 | 1.5 | 239.4 |
| 10 | 230 | 0*$^1$ | R: methyl 12.3/1 | 0.385 | 1.10 | 3270 | (R: methyl) 73.7 | (R: methyl) 84.4 | 5.2 | 182.7 |
| 11 | 220 | 0*$^1$ | R: ethyl 12.0/1 | 0.276 | 2.09 | 1720 | (R: ethyl) 79.7 | (R: ethyl) 86.6 | 6.3 | 135.7 |
| 12 | 220 | 0*$^1$ | R: butyl 12.0/1 | 0.276 | 3.07 | 1170 | (R: butyl) 78.0 | (R: butyl) 86.1 | 6.2 | 121.0 |
| 13 | 216 | 0*$^1$ | R: methyl 12.0/1 | 0.267 | 1.85 | 1950 | (R: methyl) 57.8 | (R: methyl) 80.3 | 15.7 | 95 |
| Comparative Example | | | | | | | | | | |
| 4 | 220 | 0*$^1$ | R: methyl 25.0/1 | 0.250 | 1.14 | 3170 | (R: methyl) 57.3 | (R: methyl) 69.2 | 15.4 | 76 |
| 5 | 249 | 0*$^1$ | R: methyl 25.0/1 | 0.250 | 1.09 | 3320 | (R: methyl) 36.0 | (R: methyl) 57.0 | 4.0 | 39 |

Note: (*)$_1$ . . . The ambient atmospheric pressure.

Example 14

A distilling-separation apparatus consisted of a packing type distillation column having an inside diameter of 30 mm and a height of 1000 mm and equipped with a cooling and liquid-separation device located in a top portion of the column and a side reboiler located in a bottom portion of the column, and a McMahon packing made of SUS316 filled in the column.

The pressure in the top portion of the distillation column was maintained at a level of 50 mmHg, and a preheated mixture of methyl glycolate at a feed rate of 130.9. g/hr with dimethyl oxalate at a feed rate of 19.1 g/hr was continuously fed into the distillation column through an inlet located in a middle portion thereof, and dimethyl adipate was fed at a feed rate of 30.0 g/hr into the distillation column through an inlet located in the top portion thereof. The resultant mixture was subjected to a continuous distillation at a column top temperature of 76° C. at a column bottom temperature of 110° C. at a reflux ratio of about 10.

When the distillation reached a steady state, a vapor mixture of methyl glycolate at a delivery rate of 130.8 g/hr with dimethyl oxalate at a delivery rate of 3.5 g/hr was delivered at a total delivery rate of 134.3 g/hr through a top outlet of the column, and a liquid mixture consisting of methyl glycolate at a delivery rate of 0.1 g/hr, dimethyl oxalate at a delivery rate of 15.6 g/hr and dimethyl adipate at a delivery rate of 30.0 g/hr was discharged at a total delivery rate of 45.7 g/hr through a bottom outlet of the column.

EXAMPLE 15

A distilling-separation apparatus consisted of a packing type distillation column having an inside diameter of 50 mm and a height of 1500 mm and equipped with a cooling and liquid-separation device located in a top portion of the column and a side reboiler located in a bottom portion of the column, and a McMahon packing made of SuS316 filled in the column.

The pressure in the top portion of the distillation column was maintained at a level of 50 mmHg, and a preheated mixture of methyl glycolate at a feed rate of 654.7 g/hr with dimethyl oxalate at a feed rate of 95.3 g/hr was continuously fed into the distillation column through an inlet located in a middle portion thereof, and dimethyl succinate was fed at a feed rate of 150.0 g/hr into the distillation column through an inlet located in the top portion thereof. The resultant mixture was subjected to a continuous distillation at a column top temperature of 76° C. at a column bottom temperature of 108° C. at a reflux ratio of about 5.

When the distillation reached a steady state, a vapor mixture of methyl glycolate at a delivery rate of 654.5 g/hr with dimethyl oxalate at a delivery rate of 17.5 g/hr was delivered at a total delivery rate of 671.9 g/hr through a top outlet of the column, and a liquid mixture consisting of methyl glycolate at a delivery rate of 0.3 g/hr, dimethyl oxalate at a delivery rate of 77.8 g/hr and dimethyl succatate at a delivery rate of 150.0 g/hr was discharged at a total delivery rate of 228.3 g/hr through a bottom outlet of the column.

We claim:

1. A method for producing a glycolic acid ester, comprising the steps of hydrogenating in a gas phase, an oxalic acid diester of the formula (I):

$$(COOR)_2 \qquad (I)$$

wherein R represents a lower alkyl group having 1 to 6 carbon atoms, with hydrogen in the presence of a solid catalyst and in the additional presence of a vapor of at least one aliphatic alcohol, in an amount of 5 molar parts or more per molar part of the oxalic acid diester, and collecting the resultant glycolic acid ester from the reaction mixture.

2. The method as claimed in claim 1, wherein the oxalic acid diester is selected from the group consisting of dimethyl oxalate, diethyl oxalate, dipropyl oxalate, dibutyl oxalate and diamyl oxalate.

3. The method as claimed in claim 1, wherein the solid catalyst comprises a solid carrier and a catalytic component carried on the carrier and comprising at least one member selected from copper group metals, iron group metals, and platinum group metals.

4. The method as claimed in claim 1, wherein the aliphatic alcohol is selected from aliphatic monohydric alcohols having 1 to 6 carbon atoms.

5. The method as claimed in claim 1, wherein the amount of the aliphatic alcohol is 8 to 20 molar parts per molar part of the oxalic acid diester.

6. The method as claimed in claim 1, wherein the oxalic acid diester is hydrogenated at a temperature of 100° C. to 300° C.

7. The method as claimed in claim 1, wherein the hydrogen and the oxalic acid diester are present in a molar ratio of 2:1 to 100:1.

8. The method as claimed in claim 1, wherein the solid catalyst comprises a solid carrier and a catalytic component carried on the solid carrier and in an amount of 0.01 to 50% by weight on the weight of the solid carrier.

9. The method as claimed in claim 1, wherein the solid catalyst comprises a solid carrier and a catalytic component carried on the solid carrier and comprising at least copper metal and silver metal.

10. The method as claimed in claim 3, 8 or 9, wherein the carrier for the solid catalyst comprises at least one member selected from the group consisting of silica, alumina, titania, zirconia, diatomaceous earth, zinc oxide, lanthanum oxide and activated carbon.

11. The method as claimed in claim 9, wherein the catalystic component for the solid catalyst comprises the copper metal and optionally a copper compound in an amount, in terms of copper metal, of 5 to 50% by weight and the salver metal and optionally a silver compound in an amount, in terms of silver metal, of 0.01 to 20% by weight, based on the weight of the solid carrier.

12. The method as claimed in claim 1, wherein the oxalic acid diester is dissolved in the aliphatic alcohol, the resultant solution is evaporated, and the resultant vapor is brought together with a hydrogen gas into contact with the solid catalyst.

13. The method as claimed in claim 12, wherein the oxalic acid diester dissolved in the aliphatic alcohol is in a concentration of 10 to 40% by weight.

14. The method as claimed in claim 1, wherein, in the collecting step, the resultant reaction mixture from the hydrogenating step, which comprises the resultant glycolic acid ester and a remaining fraction of non-reacted oxalic acid diester, is subjected to distillation in the presence of an ester of a dicarboxylic acid having 3 to 12 carbon atoms, to selectively distill and collect the glycolic acid ester from the reaction mixture; and a resultant distillation residue comprising a mixture of the non-reacted oxalic acid diester fraction with the ester of the dicarboxylic acid having 3 to 12 carbon atoms is withdrawn in the form a liquid from the distillation system.

15. The method as claimed in claim 14, wherein the ester of the dicarboxylic acid having 3 to 12 carbon atoms is selected from diesters of dicarboxylic acids having 3 to 12 carbon atoms with aliphatic monohydric alcohols having 1 to 4 carbon atoms.

16. The method as claimed in claim 14, wherein the dicarboxylic acids are selected from the group consisting of malonic acid, succinic acid, glutaric acid, adipic acid, pimelic acid, suberic acid, azelaic acid, brassylic acid, and dodecanedioic acid.

17. The method as claimed in claim 14, wherein in the distillation system, the ester of the dicarboxylic acid having 3 to 12 carbon atoms is present in a molar fraction of 0.1 or more based on the total molar amount of the glycolic acid ester, the oxalic acid diester and the dicarboxylic acid ester.

18. A method of producing a glycolic acid ester, comprising the steps of hydrogenating in a gas phase, an oxalic acid diester of the formula (I):

$$(COOR)_2 \qquad (I)$$

wherein R represents a lower alkyl group having 1 to 6 carbon atoms, with hydrogen in the presence of a solid catalyst comprising a solid carrier and a catalytic component carried on the solid carrier and comprising at least copper metal and silver metal and in the additional presence of a vapor comprising at least one aliphatic alcohol, in an amount of 5 molar parts or more per molar part of the oxalic acid diester, and collecting the resultant glycolic acid ester from the reaction mixture.

19. The method as claimed in claim 18, wherein the carrier for the solid catalyst comprises at least one member selected from the group consisting of silica,, alumina, titania, zirconia, diatomaceous earth, zinc oxide, lanthanum oxide and activated carbon.

20. The method as claimed in claim 18, wherein the catalystic component for the solid catalyst comprises the copper metal and optionally a copper compound in an amount, in terms of copper metal, of 5 to 50% by weight and the silver metal and optionally a silver compound in an amount, in terms of silver metal, of 0.01 to 20% by weight, based on the weight of the solid carrier.

* * * * *